United States Patent [19]
Tahara et al.

[11] 4,373,107
[45] Feb. 8, 1983

[54] PROCESS FOR PREPARING N-ALKYL-ALKYLENE-DIAMINES

[75] Inventors: Susumu Tahara; Keigo Nishihira; Takashi Miyatake; Hiroyuki Sawada, all of Ube; Junichiro Kita, Ichihara, all of Japan

[73] Assignee: Ube Industries, Ltd., Ube, Japan

[21] Appl. No.: 286,030

[22] Filed: Jul. 22, 1981

[30] Foreign Application Priority Data

Aug. 13, 1980 [JP] Japan ................................ 55/111590

[51] Int. Cl.$^3$ .............................................. C07C 85/08
[52] U.S. Cl. .................................. 564/473; 564/471; 564/472
[58] Field of Search ........................ 564/471, 472, 473

[56] References Cited

U.S. PATENT DOCUMENTS 2,317,757  4/1943  Graf .................................... 564/473
3,442,951  5/1969  Thirion ............................... 564/473

Primary Examiner—John Doll
Attorney, Agent, or Firm—Frishauf, Holtz, Goodman & Woodward

[57] ABSTRACT

A process for preparing an N-alkylene-diamine by contacting an alkylene diamine with an aliphatic aldehyde in a reaction solvent in the presence of hydrogen under pressure and an platinum group metal, which comprises gradually adding the aliphatic aldehyde to the alkylene diamine. The process according to the present invention provides a high conversion of the alkylene diamine and a high selectivity to the N-alkyl-alkylene-diamine.

13 Claims, No Drawings

PROCESS FOR PREPARING N-ALKYL-ALKYLENE-DIAMINES

The present invention relates to a process for preparing an N-alkyl-alkylene-diamine.

It is already known to prepare an N-alkyl-alkylene-diamine by adding an aliphatic aldehyde reactant all at once to an alkylene diamine under hydrogen pressure, and reacting them in the presence of a platinum group metal (U.S. Pat. No. 2,317,757). However, as noted from the Comparative examples described below, this conventional method in which the entire amount of the aliphatic aldehyde is added at the same time to an alkylene diamine can only give a low conversion of the alkylene diamine and only a low selectivity to the N-alkyl-alkylene-diamine. Thus, with this conventional method, the desired N-alkyl-alkylene-diamine can be obtained only in a low yield.

The present invention provides a process for preparing an N-alkyl-alkylene-diamine in a higher yield from an alkylene diamine and an aliphatic aldehyde.

That is, the present invention is defined as a process for preparing an N-alkyl-alkylene-diamine by contacting an alkylene diamine with an aliphatic aldehyde in a reaction solvent in the presence of hydrogen under pressure and a platinum group metal, which comprises gradually adding the aliphatic aldehyde to the alkylene diamine.

According to the present invention, the N-alkyl-alkylene-diamine can be obtained in high yield by a simple operation. Therefore, this invention is extremely valuable from an industrial point of view.

Examples of the alkylene diamines to be used in the present invention include ethylene diamine, propylene diamine, tetramethylene diamine, hexamethylene diamine, etc.

Examples of the aliphatic aldehydes to be used according to the present invention are formaldehyde, acetaldehyde, propionaldehyde, butyraldehyde, etc. Aliphatic aldehydes are preferably used in an amount of about 1 mole or less per mole of alkylene diamines, especially about 0.5 to 1 mole per mole of alkylene diamines. If aliphatic aldehydes are used in an excessively larger amount, N,N'-dialkyl-alkylene-diamines are formed as by-products in a larger amount. If the amount of alkylene diamines used is excessively small, the conversion of alkylene diamines decreases, making the process unfavourable for industrial purposes.

Platinum group metals which may be used for the present invention are for example palladium, platinum, rhodium, ruthenium, iridium, etc. Platinum group metals may also be used in a form supported, in a proportion of 0.01 to 10% by weight, on an inert carrier such as activated carbon, alumina, silica, diatomaceous earth, pumice, zeolite and molecular sieves. In general, platinum group metals are used in an amount of 0.1 to 10 grams per liter of reaction solvents.

Examples of reaction solvents which may be used for the present invention include aliphatic alcohols such as methyl alcohol, ethyl alcohol, isopropyl alcohol and n-butyl alcohol; aromatic hydrocarbons such as benzene, toluene and xylene; water, etc. Reaction solvents may be used in any amount. In general, they are used in an amount of 100 to 2,000 parts by weight per 100 parts by weight of alkylene diamines.

The hydrogen pressure to be used in the reaction system according to the present invention is, in general, 2 to 80 kg/cm$^2$ (gauge pressure). The reaction temperature used is usually 40° to 150° C., preferably 60° to 120° C.

In the process of the present invention, it is necessary to gradually add aliphatic aldehydes to alkylene diamines. It is preferable that aliphatic aldehydes are added to alkylene diamines at a rate of 0.01 to 0.5 mole/hour per mole of alkylene diamines subjected to the reaction, particularly at a rate of 0.1 to 0.3 mole/hour per mole of alkylene diamines. If aliphatic aldehydes are added at an excessively higher rate, the yield of N-alkyl-alkylene-diamines decreases. If the rate of adding aliphatic aldehydes is too low, a longer time is required for the reaction, making the process unfavourable for industrial purposes.

As, when noted hereinbefore the entire portion of aliphatic aldehydes is added all at one time to alkylene diamines, the required N-alkyl-alkylene-diamines are obtained only in a low yield.

The present invention is further illustrated by the following nonlimitative Examples as well as Comparative examples.

EXAMPLE 1

100 ml of methyl alcohol containing 45 grams of ethylene diamine, and 2 grams of activated carbon powder supporting 5% by weight of metallic palladium thereon were put into an autoclave having an internal volume of 0.5 liter.

The temperature of the contents in the autoclave was raised to 100° C. and, thereafter, hydrogen gas was introduced into the autoclave until the hydrogen pressure reached 7 kg/cm$^2$ (gauge pressure).

Then, a mixture of 37 grams of an aqueous 90 wt % acetaldehyde solution and 100 ml of methyl alcohol was added gradually over a period of 8 hours under stirring. After the addition was completed, the reaction was continued for further 4 hours. The reaction temperature was kept at 100° C., and the hydrogen pressure at 7 kg/cm$^2$ (gauge pressure).

After the reaction was completed, the unreacted ethylene diamine, product N-ethyl-ethylene-diamine and by product N,N'-diethyl-ethylene-diamine were quantitatively determined through gas chromatography. Then, the conversion of ethylene diamine and the selectivity to the products were calculated.

The results are shown in Table 1.

EXAMPLE 2

The same procedure as described in Example 1 was repeated, except that the mixture of acetaldehyde and methyl alcohol was added over a period of 4 hours and that, after the addition was completed, the reaction was continued for further 6 hours.

The results are shown in Table 1.

EXAMPLE 3

The same procedure as described in Example 1 was repeated, except that ethyl alcohol was used instead of methyl alcohol.

The results are shown in Table 1.

EXAMPLE 4

The procedure of Example 2 was repeated, except that ethyl alcohol was used instead of methyl alcohol.

The results are shown in Table 1.

COMPARATIVE EXAMPLE 1

The procedure of Example 1 was repeated, except that all of the mixture of the aqueous acetaldehyde solution and methyl alcohol was added at the same time when starting the reaction, and that the reaction time was 12 hours.

The results are shown in Table 1.

COMPARATIVE EXAMPLE 2

The procedure of Example 2 was repeated, except that all of the mixture of the aqueous acetaldehyde solution and methyl alcohol was added at the same time when starting the reaction, and that the reaction time was 10 hours.

The results are shown in Table 1.

EXAMPLE 5

100 ml of water containing 18 grams of ethylene diamine, and 2 grams of activated carbon powder supporting 5% by weight of metallic palladium thereon were put into an autoclave having an internal volume of 0.5 liter.

The temperature of the contents in the autoclave was raised to 80° C. and, thereafter, hydrogen gas was introduced into the autoclave until the hydrogen pressure reached 7 kg/cm$^2$ (gauge pressure).

Then, 315 grams of an aqueous 4.3 wt % acetaldehyde solution was added gradually over a period of 5 hours under stirring. After the addition was completed, the reaction was continued for further 3 hours. The reaction temperature was kept at 80° C., and the hydrogen pressure at 7 kg/cm$^2$ (gauge pressure).

The results are shown in Table 1.

EXAMPLE 6

The procedure of Example 5 was repeated, except that 100 ml of benzene was used instead of water put into the autoclave together with ethylene diamine, and that a solution containing 4.3% by weight of acetaldehyde in benzene was used instead of the aqueous acetaldehyde solution.

The results are shown in Table 1.

EXAMPLE 7

5 liters of methyl alcohol containing 1,620 grams of ethylene diamine, and 22 grams of activated carbon powder supporting 5% by weight of metallic palladium thereon were put into an autoclave having an internal volume of 20 liters.

The temperature of the contents in the autoclave was raised to 80° C. and, thereafter, hydrogen gas was introduced into the autoclave until the hydrogen pressure reached 7 kg/cm$^2$ (gauge pressure).

Then, a mixture of 1,300 grams of an aqueous 99 wt % acetaldehyde solution and 2,500 ml of methyl alcohol was added gradually over a period of 4 hours under stirring. After the addition was completed, the reaction was continued for further 4 hours. The reaction temperature was kept at 80° C., and the hydrogen pressure at 7 kg/cm$^2$ (gauge pressure).

The results are shown in Table 1.

In Table 1, "ED" denotes ethylene diamine, "NED" is N-ethyl-ethylene-diamine, and "NDED" is N,N'-diethyl-ethylene-diamine.

TABLE 1

|  | ED conversion (%) | Selectivity (%) | |
| --- | --- | --- | --- |
|  |  | NED | NDED |
| Example 1 | 40.9 | 78.9 | 7.3 |
| Example 2 | 21.8 | 48.3 | 5.6 |
| Example 3 | 57.2 | 84.6 | 11.2 |
| Example 4 | 27.8 | 60.6 | 2.0 |
| Comparative Example 1 | 27.6 | 24.2 | 4.2 |
| Comparative Example 2 | 38.5 | 19.8 | 2.2 |
| Example 5 | 23.8 | 92.3 | 1.0 |
| Example 6 | 24.8 | 53.5 | 11.0 |
| Example 7 | 64.6 | 71.9 | 9.8 |

We claim:

1. In the process for preparing an N-alkyl-alkylene-diamine by contacting an alkylene diamine with an aliphatic aldehyde in a reaction solvent in the presence of hydrogen under pressure and a platinum group metal, the improvement which comprises gradually adding the aliphatic aldehyde to the alkylene diamine in the absence of an alkalene substance other than said diamine.

2. The process of claim 1 wherein said aliphatic aldehyde is used in an amount of about 1 mole per mole of the alkylene diamine.

3. The process of claim 2 wherein said aliphatic aldehyde is used in an amount of about 0.5 mole to 1 mole per mole of the alkylene diamine.

4. The process of claim 1 wherein said platinum group metal is used in an amount of 0.1 to 10 grams per liter of said reaction solvent.

5. The process of claim 1 wherein said solvent is used in an amount of 100 to 2,000 parts by weight per 100 parts by weight of the alkylene diamine.

6. The process of claim 1 wherein the hydrogen pressure in the reaction system is 2 to 80 kg/cm$^2$ (gauge pressure).

7. The process of claim 1 wherein the reaction is carried out at a temperature of 40° to 150° C.

8. The process of claim 7 wherein the reaction is conducted at a temperature of 60° to 120° C.

9. The process of claim 1 wherein said aliphatic aldehyde is added to the alkylene diamine at a rate of 0.01 to 0.5 mole/hour per mole of the alkylene diamine.

10. The process of any one of claims 2, 4, 5, 6 or 8 wherein said aliphatic aldehyde is added to the alkylene diamine at a rate of 0.1 to 0.3 mole/hour per mole of the alkylene diamine.

11. The process of claim 1 wherein (i) said aliphatic aldehyde is used in an amount of from about 1 mole per mole of the alkylene diamine, (ii) said platinum group metal is used in an amount of from 0.1 to 10 grams per liter of said reaction solvent, (iii) said reaction solvent is used in an amount of from 100 to 2,000 parts by weight per 100 parts by weight of the alkylene diamine, (iv) the hydrogen pressure in the reaction system is 2 to 80 kg/cm$^2$ (gauge pressure), (v) the reaction is carried out at a temperature of from 40° to 150° C., and (vi) said aliphatic aldehyde is added to the alkylene diamine at a rate of from 0.1 to 0.5 mole/hour per mole of the alkylene diamine.

12. The process of claim 11 wherein said aliphatic aldehyde is added to the alkylene diamine at a rate of 0.1 to 0.3 mole/hour per mole of the alkylene diamine.

13. The process of claim 12 wherein said aliphatic aldehyde is used in an amount of about 0.5 mole to 1 mole per mole of the alkylene diamine, and wherein the reaction is carried out at a temperature of 60° to 120° C.

* * * * *